(12) United States Patent
Hernandez

(10) Patent No.: US 11,160,724 B2
(45) Date of Patent: Nov. 2, 2021

(54) VIBROTACTILE STIMULATION DEVICE

(71) Applicants: INSERM (INSTITUT NATIONAL DE LA SANTE ET DE LA RECHERCHE MEDICALE), Paris (FR); UNIVERSITE DE RENNES I, Rennes (FR)

(72) Inventor: Alfredo Hernandez, Cesson-sevigne (FR)

(73) Assignees: UNIVERSITE DE RENNES I, Rennes (FR); INSERM (INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 660 days.

(21) Appl. No.: 15/529,190

(22) PCT Filed: Nov. 24, 2015

(86) PCT No.: PCT/IB2015/059083
§ 371 (c)(1),
(2) Date: May 24, 2017

(87) PCT Pub. No.: WO2016/083998
PCT Pub. Date: Jun. 2, 2016

(65) Prior Publication Data
US 2017/0326024 A1 Nov. 16, 2017

(30) Foreign Application Priority Data
Nov. 24, 2014 (FR) ...................................... 14/61377

(51) Int. Cl.
*A61H 23/02* (2006.01)
*A61B 5/00* (2006.01)

(52) U.S. Cl.
CPC ........... *A61H 23/02* (2013.01); *A61B 5/0051* (2013.01); *A61B 5/442* (2013.01); *A61B 5/4818* (2013.01);
(Continued)

(58) Field of Classification Search
CPC .............. A61H 23/02; A61H 2201/165; A61B 5/68335; A61B 5/0051; A61B 5/4818; A61B 5/4836; A61F 5/01
See application file for complete search history.

(56) References Cited

U.S. PATENT DOCUMENTS

| 5,035,242 A | 7/1991 | Franklin et al. |
| 5,195,532 A * | 3/1993 | Schumacher ........ A61B 5/0051 600/552 |

(Continued)

FOREIGN PATENT DOCUMENTS

| EP | 2474339 | 7/2012 |
| EP | 2313151 | 8/2013 |

(Continued)

OTHER PUBLICATIONS

Sophia, Katherine; Jones, Lynette; "Mechanical and Psychophysical Studies of Surface Wave Propagation during Vibrotactile Stimulation"; Jul.-Sep. 2013; IEEE Transactions on Haptics, vol. 6, No. 3, pp. 320-329. (Year: 2013).*

(Continued)

*Primary Examiner* — Samchuan C Yao
*Assistant Examiner* — Nathan M Le
(74) *Attorney, Agent, or Firm* — Brooks Kushman P.C.

(57) ABSTRACT

A vibrotactile stimulation device intended to be applied against a body environment (MC) to be stimulated and having a vibrating effector suitable for applying, to the environment, pulses of mechanical vibrational energy, and a controller controlling the effector according to stimulation (Continued)

rules. The device further includes vibration detector suitable for being exposed to the body environment in order to receive a part of the vibrational energy transmitted to the environment during the application of the pulses of vibrational energy, and determine a transmission characteristic of the vibrational energy between the effector and the environment to be stimulated, the vibration detector being linked to the controller. An application to improving the efficacy of body stimulation in combating sleep apnea is also disclosed.

11 Claims, 1 Drawing Sheet

(52) U.S. Cl.
CPC .......... *A61B 5/4836* (2013.01); *A61B 5/6843* (2013.01); *A61B 5/68335* (2017.08); *A61B 5/6833* (2013.01); *A61B 2562/0219* (2013.01); *A61H 2201/0188* (2013.01); *A61H 2201/1604* (2013.01); *A61H 2201/164* (2013.01); *A61H 2201/165* (2013.01); *A61H 2201/1619* (2013.01)

(56) References Cited

U.S. PATENT DOCUMENTS

| | | |
|---|---|---|
| 5,555,891 A | 9/1996 | Eisenfeld |
| 6,213,955 B1 | 4/2001 | Karakasoglu et al. |
| 6,265,978 B1 | 7/2001 | Atlas |
| 6,275,213 B1 | 8/2001 | Tremblay et al. |
| 6,748,275 B2 | 6/2004 | Lattner et al. |
| 8,532,761 B2 | 9/2013 | De Vos et al. |
| 2002/0029924 A1 | 3/2002 | Courage |
| 2002/0068870 A1* | 6/2002 | Alam .................. A61B 5/0051 600/446 |
| 2003/0220556 A1* | 11/2003 | Porat .................. A61B 5/0051 600/407 |
| 2004/0210261 A1 | 10/2004 | King et al. |
| 2007/0118011 A1* | 5/2007 | Harrison .............. H04R 25/456 600/25 |
| 2007/0232962 A1 | 10/2007 | Zumeris et al. |
| 2008/0103545 A1* | 5/2008 | Bolea .................. A61N 1/37229 607/42 |
| 2010/0256460 A1 | 10/2010 | Haveri et al. |
| 2011/0166619 A1 | 7/2011 | de Vos |
| 2013/0030259 A1 | 1/2013 | Thomsen et al. |
| 2013/0102937 A1 | 4/2013 | Ehrenreich et al. |
| 2013/0197321 A1 | 8/2013 | Wilson |
| 2014/0046166 A1 | 2/2014 | Tokita |
| 2014/0180036 A1 | 6/2014 | Bukkapatnam et al. |
| 2014/0206977 A1 | 7/2014 | Bahney et al. |

FOREIGN PATENT DOCUMENTS

| | | |
|---|---|---|
| FR | 2908624 | 5/2008 |
| WO | 0066215 | 11/2000 |
| WO | 2007141345 | 12/2007 |
| WO | 2007147046 | 12/2007 |
| WO | 2008072948 | 6/2008 |
| WO | 2009082682 | 7/2009 |
| WO | 2009154458 A2 | 12/2009 |
| WO | 2009154458 A3 | 12/2009 |

OTHER PUBLICATIONS

International Search Report for PCT/IB2015/059083, English translation attached to original, Both completed by the European Patent Office dated Mar. 2, 2016, All together 7 pages.

Pichardo et al. Proceedings of the IEEE 27th Annual Northeast Bioengineering Conference 2001, 2 Pages, "Validation of a Vibrotactile Stimulation System to Treat Apnea of Prematurity".

Website http://www.nichd.nih.gov/cochrane_data/osbornd_05/osbornd_05.html Osborn et al, Dated Jan. 28, 2014, 8 Pages, Cochrane Neonatal Reviews, "Kinesthetic stimulation for treating apnea in preterm infants".

* cited by examiner

VIBROTACTILE STIMULATION DEVICE

CROSS-REFERENCE TO RELATED APPLICATION

This application is the U.S. national phase of PCT Application No. PCT/I132015/059083 filed on Nov. 24, 2015, which claims priority to French Patent Application No. 14/61377 filed on Nov. 24, 2014, the disclosures of which are incorporated in their entirety by reference herein.

FIELD OF THE INVENTION

The present invention concerns vibrotactile or kinesthesic stimulation devices in general.

PRIOR ART

Vibrotactile or kinesthesic stimulation is known in the prior art and has been used routinely for more than 20 years in various fields of application, especially for sensory assistance.

Thus, document U.S. Pat. No. 5,035,242 A concerns a stimulation device for the hearing impaired, and document WO 2009082682 A1 proposes a device for those with visual impairments.

Vibrotactile stimulation is also used for the treatment of sleep apnea, especially in premature newborns (see in particular U.S. Pat. No. 5,555,891 A or WO2007141345 A1).

Several transducer principles are used in vibrotactile or kinesthesic effectors. In the vast majority, these provide a mechanical stimulation by the application of an electric signal of predefined characteristics.

Regardless of the type of electromechanical transduction used, the mechanical energy produced by the effector is transmitted into the target environment (skin, bone, etc.) in a manner which is largely dependent on the quality of the coupling between the effector and said target environment.

Thus, a stimulation device parametrized to apply a given energy stimulation is liable to deliver insufficient energy to the target environment to achieve the desired effect, on account of a poor quality of coupling, which in some cases may result in a dramatic prolongation of an apnea phase for the patient. More generally, given the uncertainties as to the quality of the coupling, the stimulation system cannot guarantee that it has effectively delivered the desired therapy.

Document US2013102937A3 describes a device for the treatment of hypertension, where a vibrational treatment is applied in certain regions. An impedance sensor is provided to indicate whether the device has been properly placed on the body of the user. Besides the fact that this document does not relate to the treatment of sleep disorders, it makes use of an electrical detection principle (impedance detection) which also is not able to reveal with certainty whether the vibrations, which are mechanical in nature, are properly applied to the intended region of the body.

SUMMARY OF THE INVENTION

The present invention intends to propose a vibrotactile stimulation device, especially but not exclusively for the treatment of sleep apnea, which is able to estimate in a realistic manner the quality of the mechanical coupling to the target environment, and if necessary adjust the vibrotactile energy provided by the effector to achieve the effect required on the patient.

Thus, according to the invention, a vibrotactile stimulation device is proposed, especially to effect a bodily stimulation in the fight against sleep apnea, designed to be applied against a body environment to be stimulated and comprising a vibrating effector able to apply to said environment pulses of mechanical vibrational energy, and means of control of the effector depending on the rules of stimulation, the device being characterized in that it also comprises detector means able to be exposed to the body environment in order to receive a portion of vibrational energy transmitted to these means by said environment during the application of the pulses of vibrational energy, and to determine a characteristic of transmission of the vibrational energy between the effector and the environment to be stimulated, said detector means being connected to the control means.

One may supplement these characteristics with the following preferred yet optional characteristics, taken in every combination which the person skilled in the art might find to be technically compatible.

- the device further comprises means of adjusting the energy transmitted by the effector as a function of said characteristic of transmission.
- the effector and the detector means are received inside a common unit.
- the detector means comprise an accelerometer.
- the detector means are able to effect a kinematic detection along an axis corresponding to a preferred axis of vibration of the effector.
- the effector is able to transmit a vibrational energy along a principal axis perpendicular to an interface between the effector and the environment to be stimulated.
- the accelerometer is an accelerometer with at least two axes, one of which is generally parallel to said principal axis.
- the device comprises means able, in response to the signals provided by the detector means, to provide information as to correct and/or incorrect placement of the device on the environment to be stimulated.
- the device comprises a plate carrying its various elements, and a disposable flexible casing able to receive the plate in a removable manner.
- the collection of elements carried by the plate are encapsulated.
- the flexible casing comprises features able to receive and hold elastically at least part of the edge of the device.
- said casing has a peripheral edge provided with an adhesive.

BRIEF DESCRIPTION OF THE DRAWINGS

Other aspects, purposes and advantages of the present invention will appear better upon perusal of the following detailed description of a preferred embodiment thereof, given as a nonlimiting example and making reference to the enclosed drawings, in which.

DETAILED DESCRIPTION OF A PREFERRED EMBODIMENT

Figure 1:
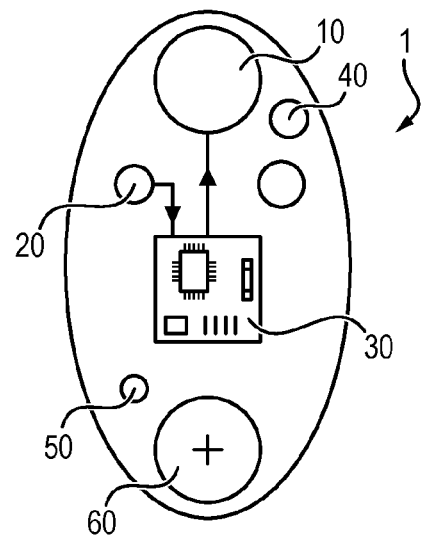
FIG. 1 is a schematic front view of a vibrotactile stimulation device, designed to be placed behind the ear of a patient, and the various elements making up this device.

Referring to the drawings, a vibrotactile or kinesthesic stimulation device 1 according to the invention basically comprises an electromechanical vibrational effector or exciter 10 and a movement sensor 20.

In a preferred manner, the effector 10 comprises a piezo-electric element or a linear resonant actuator, whereas the sensor 20 comprises an accelerometer, preferably a triaxial accelerometer. This device likewise comprises on-board digital processing means 30, typically in the form of an electronic card provided with a microcontroller, designed to process the stimulation signals applied to the effector and the signals received by the sensor 20 in order to estimate the quality of the coupling between the effector and the target environment MC (in the present instance, the subcutaneous region of the patient behind an ear) and thus the efficacy of the mechanical energy delivered by the effector to the target environment.

The device may have other functionalities. For example, it may integrate a temperature sensor 40 providing temperature signals, either analog and converted into digital signals at the processing device or directly digital, a light (LED) and/or sonic (vibrator) signaling device 50 indicating the state of the device, an on/off switch, etc.

It is energized by a button cell 60 having an appropriate capacity, or optionally by a rechargeable battery, in a wired manner (for example, to the USB port of a computer) or wirelessly (by inductive power transmission, in a manner known per se for small electronic appliances).

According to a variant embodiment, the digital processing means, or a portion of these processing means, may be moved to a separate box of the device and either be carried by the patient or arranged in proximity to the patient, for example, on their nightstand, during sleep.

Means of transmission are then provided to enable the communication of the device with the remote box, these means being either wire-line or wireless for a box carried by the patient, and preferably wireless for a fixed box.

Figure 2:
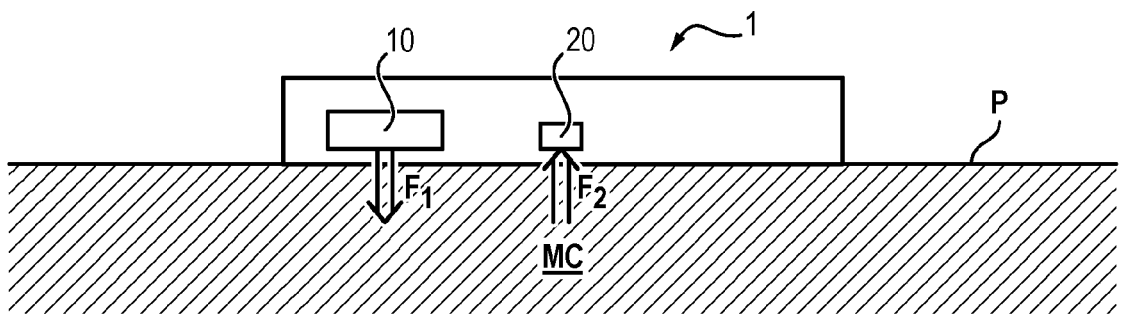
FIG. 2 is a schematic and partial cross sectional view of the device of FIG. 1.

Referring more particularly to FIG. 2, the device is able to emit, depending on criteria such as the detection of a sleep apnea phenomenon by means not described here and possibly being conventional means (such as the detection of a respiratory air flow or a respiratory movement), mechanical excitatory pulses with the aid of the effector 10. These pulses for example have a frequency of the order of 100 to 400 Hz, and are controlled by the control circuit 30 in response to the detection signals received via a wire-line or wireless interface, not shown.

The arrow F1 illustrates the vibrational mechanical energy transmitted to the environment MC, comprising a principal component perpendicular to the physical interface between the device and the environment, but also the components of weaker amplitude, in the two dimensions of the plane of this interface.

A portion of this vibrational energy is dispersed laterally by the environment MC, and the arrow F2 illustrates a fraction of this energy situated at right angles to the sensor 20. This latter collects a signal, provided to the circuit 30, which is representative of the way in which the environment MC has modified the vibrational mechanical energy injected by the effector.

It will be understood that the amplitude and the frequency content of the signal collected by the sensor 20 depend directly on the quality of the coupling between the effector 10 and the environment MC. In fact, the environment MC can be viewed as a transfer function, linear or nonlinear, between the input signal (signal of stimulation) and the signal collected by the sensor 20. The circuit 30 thus has information regarding the quality of this coupling in real time or quasi-real time. It is thus capable, in particular:

of modulating the parameters of the signal applied to the effector 10, and especially of amplifying the vibrational pulses in the event of a poor coupling; for example, one may implement a simple mathematical law consisting in boosting the energy applied by the effector by a factor of 1/X for a transmission rate X (less than 1 and measured in relation to the transmission by an "ideal" medium);

of detecting and signaling, for example with the aid of the signaling device 50, that the device is poorly coupled to the environment, by detecting that the energy picked up in the area of the arrow F2, for an energy injected into the environment along the arrow F1, is less than a certain threshold.

It should also be noted that the measurement of the energy propagated by the environment MC with the aid of the accelerometric detector 20 may provide the user with an indication of correct placement of the device 1. In particular, one may arrange that the device, after being put in place and started in operation (for example, with the help of an on/off button) generates a pulse train of given energy, and only validates the placement when the energy collected at the sensor 20 is above a certain threshold, or above a certain minimum threshold and below a certain maximum threshold.

It will likewise be noted that the detection of the coupling between the device 1 and the target environment MC and/or the detection of a correct placement may be done, or made more accurate, by likewise utilizing the amplitude and frequency content values of the vibrational signals collected by the sensor 20 along the two axes (denoted x and y) contained in the plane of the device/environment interface, in addition to the amplitude and frequency content value along the perpendicular axis z.

In particular, it has been observed that the transmission of the vibrational energy in the form of surface waves varies in a way which is quite representative of the pressure exerted by the effector 10 on the target environment, in the present case, the surface of the skin.

The dimensions of the device are typically from 3 to 8 cm along the major axis and from 2 to 6 cm along the minor axis, and the distance between the axis of the effector 10 and the axis of the sensor 20 is preferably between 0.5 and 3 cm to avoid too much dispersion of the energy transmitted. However, these values are in no way limiting.

Figure 3:
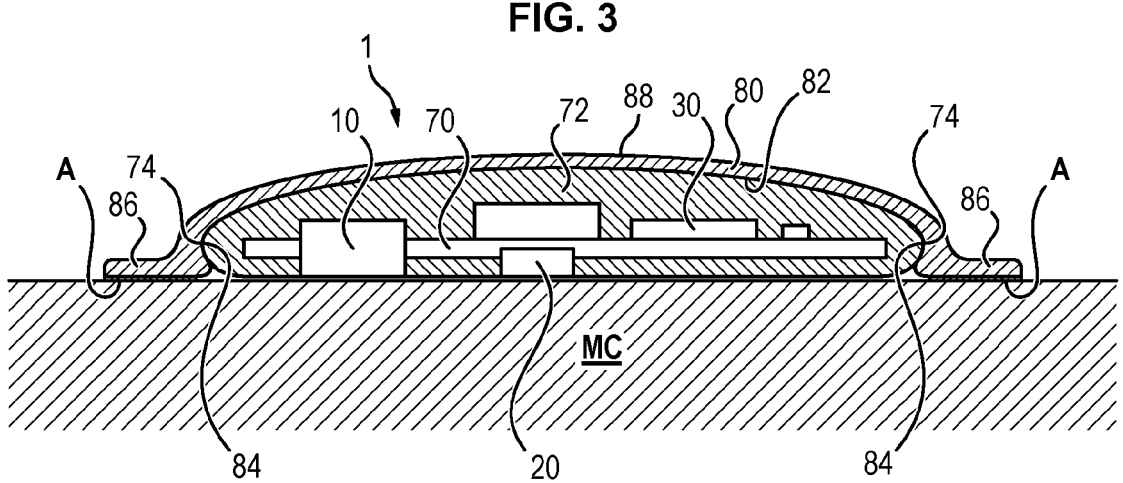
FIG. 3 is a cross sectional view of an example of practical implementation of the device of FIGS. 1 and 2.

FIG. 3 illustrates a practical implementation of the device according to the invention. The various elements of the device are mounted on the plate 70, the whole being encased in a resin block or shell 72 having peripheral edges 74 suitable for coupling with a means of fixation on the skin. Such a means of fixation may be a disposable casing 80, made of an elastic material and able to receive the device in an internal cavity 82, holding it by the edges 74 of the encapsulating resin block, which are engaged in a peripheral notch 84 of said casing.

A biocompatible adhesive A may be provided at the peripheral edge 86 of said casing, designed to be in contact with the skin, while a top wall 88 of the casing covers and entirely seals the device encapsulated in its resin block 72.

It will be understood that the encapsulated device 1 may be easily extracted from the casing 80 in order to replace it with a new casing. The adhesive A may be covered, in a manner known per se, by a protective film which can be peeled off prior to use.

The stimulation device according to the invention can be secured to any adapted site (behind the ear, on the lateral chest, the sole of the feet, etc.), the casing 80 and its characteristics being then adapted to the intended use.

FIG. 3 shows that the base of the device, where the effector 10 and the sensor 20 emerge, is in contact with the surface of the environment to be stimulated, in the present case the skin, via the material of the shell 72, which is chosen to assure an appropriate mechanical coupling with the environment MC.

Of course, the invention is in no way limited to the embodiment described and represented, but rather the person skilled in the art will be able to add many variants and modifications to it.

In particular:

the effector 10 and the sensor 20 may be provided on the same unit or on two different units provided in proximity to each other at the site to be stimulated;

it is possible to use the signals provided by the sensor 20, especially when it is a triaxial accelerometer, to determine the position of the implantation site, and especially the orientation of the head of the subject when the device is placed behind the ear; this advantageously allows an adapting of the stimulation strategies, especially for the treatment of sleep apnea, as a function of the characteristics of the apnea phenomena encountered and/or the position of the patient; a gyroscope can provide the same functionality in one variant;

one may add to the device any independent functionality or one correlated with the vibrational stimulation, and especially any detection or sensing of a biological parameter, besides the temperature measurement;

upon detecting an unsatisfactory coupling between the effector and the environment to be stimulated, one may arrange to adjust not only the energy of the pulses of mechanical vibrational energy, but also other parameters such as their waveform or their frequency.

The invention claimed is:

1. A vibrotactile stimulation device, designed to be applied against a body environment to be stimulated, the device comprising: a
   vibrating effector able to apply pulses of mechanical vibrational energy to said body environment,
   a controller configured to operate the vibrating effector using rules of stimulation, and
   a vibration detector arranged laterally with respect to a principal axis of the vibrating effector and adapted to be directly exposed to the body environment in order to receive a portion of vibrational energy transmitted to the vibration detector via said body environment during the application of the pulses of vibrational energy by said vibrating effector, and to determine a characteristic of transmission of the vibrational energy coupling between the vibrating effector and the body environment to be stimulated, wherein
   the vibration detector is connected to the controller for controlling said vibrating effector for selectively amplifying the pulses of mechanical vibrational energy as a function of the determined characteristic of transmission, wherein
   the controller is configured to modulate parameters of the pulses of mechanical vibrational energy applied by the vibrating effector as the function of the determined characteristic of transmission and to amplify the pulses of mechanical vibrational energy in an event of a poor coupling between the vibrating effector and the body environment.

2. The device as claimed in claim 1, wherein the vibrating effector and the vibration detector are received inside a common unit.

3. The device as claimed in claim 1, wherein the vibration detector comprises an accelerometer.

4. The device as claimed in claim 1, wherein the vibration detector is adapted to effect a kinematic detection along an axis corresponding to said principal axis of vibration of the vibrating effector.

5. The device as claimed in claim 1, wherein the vibrating effector is able to transmit the vibrational energy along the principal axis perpendicular to an interface between the vibrating effector and the body environment to be stimulated.

6. The device as claimed in claim 3, wherein the vibration detector is an accelerometer with at least two axes, one of which is generally parallel to said principal axis.

7. The device as claimed in claim 1, further comprising an indicator which in response to signals provided by the vibration detector, provides information as to correct and/or incorrect placement of the device on the body environment to be stimulated.

8. The device as claimed in claim 1, further comprising:
   a plate carrying said vibrating effector, said controller and said vibration detector, and
   a disposable flexible casing adapted to elastically receive the plate in a removable manner.

9. The device as claimed in claim 8, wherein said vibrating effector, said controller and said vibration detector carried by the plate are encapsulated.

10. The device as claimed claim 8, wherein the disposable flexible casing comprises features able to receive and removably elastically hold at least part of an edge of the plate.

11. The device as claimed in claim 8, wherein said disposable flexible casing has a peripheral edge provided with an adhesive for attachment to the body environment to be stimulated.

* * * * *